US009310339B2

(12) United States Patent
Bossi et al.

(10) Patent No.: US 9,310,339 B2
(45) Date of Patent: Apr. 12, 2016

(54) HYBRID INSPECTION SYSTEM AND METHOD EMPLOYING BOTH AIR-COUPLED AND LIQUID-COUPLED TRANSDUCERS

(75) Inventors: Richard H. Bossi, Renton, WA (US); Gary E. Georgeson, Federal Way, WA (US); Hong H. Tat, Redmond, WA (US)

(73) Assignee: The Boeing Company, Chicago, IL (US)

( * ) Notice: Subject to any disclaimer, the term of this patent is extended or adjusted under 35 U.S.C. 154(b) by 1069 days.

(21) Appl. No.: 12/182,572

(22) Filed: Jul. 30, 2008

(65) Prior Publication Data

US 2010/0024559 A1     Feb. 4, 2010

(51) Int. Cl.
| | |
|---|---|
| G01N 29/06 | (2006.01) |
| G01N 29/04 | (2006.01) |
| G01N 29/22 | (2006.01) |
| G01N 29/265 | (2006.01) |
| G01N 29/28 | (2006.01) |

(52) U.S. Cl.
CPC ............ G01N 29/043 (2013.01); G01N 29/225 (2013.01); G01N 29/265 (2013.01); G01N 29/28 (2013.01); G01N 2291/048 (2013.01); G01N 2291/102 (2013.01); G01N 2291/2694 (2013.01)

(58) Field of Classification Search
CPC . G01N 29/043; G01N 29/225; G01N 29/265; G01N 29/28; G01N 2291/2694; G01N 2291/048; G01N 2291/102
USPC ........... 73/644, 634, 635, 639, 640, 641, 643, 73/649; 310/309; 367/181
See application file for complete search history.

(56) References Cited

U.S. PATENT DOCUMENTS

| | | | |
|---|---|---|---|
| 3,028,752 A * | 4/1962 | Bacon | 73/642 |
| 4,033,178 A * | 7/1977 | Holt et al. | 73/644 |
| 6,722,202 B1 | 4/2004 | Kennedy et al. | |
| 6,862,936 B2 * | 3/2005 | Kenderian et al. | 73/636 |
| 6,945,114 B2 * | 9/2005 | Kenderian et al. | 73/643 |
| 7,030,536 B2 * | 4/2006 | Smith et al. | 310/309 |
| 7,228,741 B2 | 6/2007 | Georgeson et al. | |
| 7,231,826 B2 | 6/2007 | Bossi et al. | |

(Continued)

FOREIGN PATENT DOCUMENTS

| | | |
|---|---|---|
| EP | 1 336 842 A2 | 8/2003 |
| GB | 1 410 211 A | 10/1975 |

OTHER PUBLICATIONS

International Search Report for PCT/US2009/048442 mailed Dec. 3, 2009.

(Continued)

*Primary Examiner* — J M Saint Surin
(74) *Attorney, Agent, or Firm* — Alston & Bird LLP

(57) ABSTRACT

A hybrid inspection system and method are provided which utilize both an air-coupled transducer and a liquid-coupled transducer in order to enjoy the advantages offered by both types of transducers. The hybrid inspection system may include a first probe that includes the air-coupled transducer, such as a capacitive machined ultrasonic transducer, which is configured to emit ultrasonic signals and to air couple the ultrasonic signals into a workpiece. The hybrid inspection system may also include a second probe that includes the liquid-coupled transducer, such as a piezoelectric transducer, configured to receive the ultrasonic signals emitted by the air-coupled transducer of the first probe via a liquid coupling between the transducer and the workpiece.

20 Claims, 4 Drawing Sheets

(56) References Cited

U.S. PATENT DOCUMENTS

| | | | |
|---|---|---|---|
| 7,303,530 B2 * | 12/2007 | Barnes et al. | 600/459 |
| 7,313,959 B2 | 1/2008 | Georgeson et al. | |
| 7,320,249 B2 | 1/2008 | Georgeson et al. | |
| 7,395,714 B2 * | 7/2008 | Georgeson et al. | 73/634 |
| 7,545,075 B2 * | 6/2009 | Huang et al. | 310/309 |
| 2006/0053892 A1 | 3/2006 | Georgeson et al. | |
| 2007/0180916 A1 * | 8/2007 | Tian et al. | 73/649 |
| 2008/0139943 A1 * | 6/2008 | Deng et al. | 600/459 |

OTHER PUBLICATIONS

Xuefeng Wang, Ying Fan, Wei-Cheng Tian, Hyon-Jin Kwon, Stacey Kennerly, Glenn Claydon, Andrew May, *Development Of Air-Coupled Ultrasound Transducers For Nondestructive Evaluation*, *IEEE*, MEMS 2008, Tucson, AZ, USA, pp. 932-935, Jan. 13-17, 2008.

* cited by examiner

HYBRID INSPECTION SYSTEM AND METHOD EMPLOYING BOTH AIR-COUPLED AND LIQUID-COUPLED TRANSDUCERS

FIELD OF THE INVENTION

Embodiments of the present invention relate generally to inspection systems and methods and, more particularly, to inspection systems and methods configured to perform the nondestructive evaluation (NDE) of a workpiece.

BACKGROUND OF THE INVENTION

Non-destructive inspection (NDI)/non-destructive evaluation (NDE) (hereinafter referred to individually and/or collectively as NDE) of structures involves thoroughly examining a structure without harming the structure or requiring significant disassembly of the structure. Non-destructive inspection may be advantageous to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or inconsistencies in the structure. Inspection may be performed during manufacturing of a structure and/or once a structure is in-service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that may be non-destructively tested are composite structures, such as composite sandwich structures and other adhesive bonded panels and assemblies. In this regard, composite structures are used throughout the aircraft industry because of the engineering qualities, design flexibility and low weight of composite structures, such as the stiffness-to-weight ratio of a composite sandwich structure. As such, it may be desirable to inspect composite structures to identify any anomalies, such as cracks, voids or porosity, which could adversely affect the performance of the composite structure. For example, anomalies in composite sandwich structures, generally made of one or more layers of lightweight honeycomb or foam core material with composite or metal skins bonded to the opposed sides of the core, may include disbonds which occur at the interfaces between the core and the skin or between the core and a septum intermediate skin.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar anomalies and porosity, and/or crack detection in the structure. Resonance, pulse echo or mechanical impedance sensors may be used to provide indications of voids or porosity, such as in adhesive bondlines of the structure. High resolution inspection of aircraft and other structures may be performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as TTU transducers, is typically processed by a processing element, and the processed data may be presented to a user via a display.

In order to couple the ultrasonic signals into the structure under inspection, a couplant may be utilized between the transducer and the surface of the structure. In TTU systems having both a transmission-side transducer and a receiver-side transducer, a couplant may be disposed between each of the transducers and the respective surfaces of the structure. In order to couple sufficient energy into the structure to permit the structure to be inspected with a desired sensitivity, TTU systems may utilize water as the couplant. While the water may effectively couple the ultrasonic signals into the structure under inspection, a water delivery and removal system must be provided in order to deliver the water to the space between the transducer and the surface of the structure and to collect the excess or unused water. Not only do such water delivery and removal systems add to the expense of an NDE system, but a water delivery and removal system may make the positioning and movement of a water-coupled NDE system more cumbersome.

Further, it may be undesirable for some structures to be placed into contact with water, thereby limiting the usefulness of a water-coupled NDE system for the evaluation of such workpieces. In this regard, it may be desirable to inspect workpieces during manufacture such that the workpiece is in an incomplete form, such as a partially cured laminate or a honeycomb or foam core prior to the application of a skin thereto. Although the NDE of such incomplete structures may be desirable, it may not be advisable to expose such incomplete structures to water since the water may have an adverse impact upon the partially cured laminate or the honeycomb or foam core. Thus, water-coupled NDE techniques are not generally practical in conjunction with the inspection of such incomplete structures.

As noted above, the water delivery and removal system can make the positioning and movement of a water-coupled NDE system more cumbersome. Moreover, in some instances, at least one of the transmission-side transducer or the receiver-side transducer must be relatively small, such as in order to be inserted through a relatively small opening and/or to be moved along an interior surface of a structure in which little room is provided for movement of the TTU unit. For example, there is interest in surgical NDE systems in which at least one of the TTU units is inserted through a relatively small opening and is then moved through a relatively small space with limited accessibility. In these applications, a water couplant may be unworkable since it may be difficult, if not impossible, to both appropriately deliver and remove the water in instances in which the transducer is internal to the workpiece.

Air-coupled TTU inspection systems have also been developed in which the transmitter-side transducer and the receiver-side transducer are coupled via a layer of air to the workpiece. For ultrasonic signals, however, air does not couple the signals as efficiently as does water due to the substantial mismatch in acoustic impedance between the air and the materials of the transducer and the workpiece which leads to high interfacial reflection and low acoustic transmission efficiency. As such, in order to air-couple ultrasonic signals having sufficient energy into a workpiece such that resulting signals could be reliably detected by the receiver-side transducer, the ultrasonic signals were of a relatively low frequency, such as about 50 kHz, and therefore had only limited sensitivity. As a result of the limited sensitivity, the use of such air-coupled NDE systems is of marginal, or no, use for the inspection of workpieces that require greater sensitivity, such as during manufacturing operations and/or during in-service inspections.

It would therefore be desirable to provide improved NDE techniques including NDE techniques that rely upon the through transmission of ultrasonic signals. In particular, it would be desirable to provide for improved TTU inspection techniques that facilitate the inspection of workpieces that have at least one surface of limited accessibility, thereby facilitating the surgical NDE of a workpiece. It would also be desirable to provide for improved TTU inspection without exposing the workpieces to water, which may be deleterious to the workpiece or at least complicate further processing of the workpiece.

BRIEF SUMMARY OF THE INVENTION

A hybrid inspection system and method are therefor provided according to embodiments of the present invention which utilize both an air-coupled transducer and a liquid-coupled transducer so as to provide for an improved NDE of at least some workpieces. As such, the hybrid inspection system and method may enjoy the advantages offered by air-coupled transducers, such as the relative ease of movement, the ability to inspect workpieces within regions of limited accessibility, and the ability to inspect workpieces that are preferably not exposed to water or other liquids. However, by also employing a liquid-coupled transducer, the frequency of the ultrasonic signals can be relatively high in accordance with one embodiment, such as about one MHz or higher, such that the resulting NDE has sufficient sensitivity so as to be meaningful.

According to one embodiment, an inspection system is provided that includes first and second probes, with the first probe being configured to emit ultrasonic signals into a workpiece and a second probe being configured to receive the ultrasonic signals emitted by the first probe following propagation through the workpiece. One of the first and second probes includes an air-coupled transducer, while the other probe includes a liquid-coupled transducer. As such, ultrasonic signals propagate through air between the air-coupled transducer and the workpiece, while the ultrasonic signals propagate through liquid between the liquid-coupled transducer and the workpiece. By employing an air-coupled transducer, the inspection system of this embodiment can more readily inspect surfaces of a workpiece that have limited accessibility or may be damaged by exposure to liquid. However, by also including a liquid-coupled transducer, the inspection system of this embodiment permits a workpiece to be evaluated at a relatively high frequency, such as one MHz or higher, such that the resulting evaluation is of a desired sensitivity.

In one embodiment, the first probe includes the air-coupled transducer, which is configured to emit ultrasonic signals and to air couple the ultrasonic signals into the workpiece. In this embodiment, the second probe includes the liquid-coupled transducer configured to receive the ultrasonic signals emitted by the air-coupled transducer of the first probe via a liquid coupling between the transducer and the workpiece.

The air-coupled transducer may be a capacitive machined ultrasonic transducer. In this regard, the capacitive machined ultrasonic transducer may include an array of micromachined cells. Regardless of its configuration, the air-coupled transducer of the first probe may be configured to emit ultrasonic signals having a frequency of at least one MHz into the workpiece. The liquid-coupled transducer may include a piezoelectric transducer.

The first and second probes may each include magnets such that the first and second probes may be configured to be magnetically coupled to one another. In one embodiment, the second probe includes a mechanical connection to a scanning system so as to be driven to a plurality of positions relative to the workpiece. In this embodiment, the first probe may be without an independent motive force such that the first probe passively follows the second probe.

According to another embodiment, an inspection method is provided that emits ultrasonic signals from a first probe positioned proximate a first surface of a workpiece. In this regard, the ultrasonic signals that are emitted may have a frequency of at least one MHz. The inspection method of this embodiment air couples the ultrasonic signals from the first probe to the workpiece. The ultrasonic signals may then be received at a second probe positioned proximate a second surface of the workpiece, opposite the first surface, following propagation through the workpiece. In order to facilitate receipt of the ultrasonic signals, the ultrasonic signals may be liquid-coupled from the second surface of the workpiece.

In one embodiment, the method also initially provides the first probe having a capacitive machined ultrasonic transducer, and the second probe having a piezoelectric transducer. A liquid couplant may be provided between the piezoelectric transducer and the second surface of the workpiece, at least while the ultrasonic signals from the first probe are received.

The method of one embodiment may also magnetically couple the first and second probes. As such, by moving the second probe to a plurality of inspection positions relative to the workpiece, the first probe may be correspondingly moved since the first probe of this embodiment passively follows the second probe as a result of the magnetic coupling therebetween. As a result of its passive movement and reliance upon air coupling, the first probe may be positioned proximate a workpiece surface that may suffer if exposed to liquid and/or that is relatively inaccessible, thereby advantageously permitting TTU inspection of the workpiece.

BRIEF DESCRIPTION OF THE SEVERAL VIEWS OF THE DRAWINGS

Figure 1:
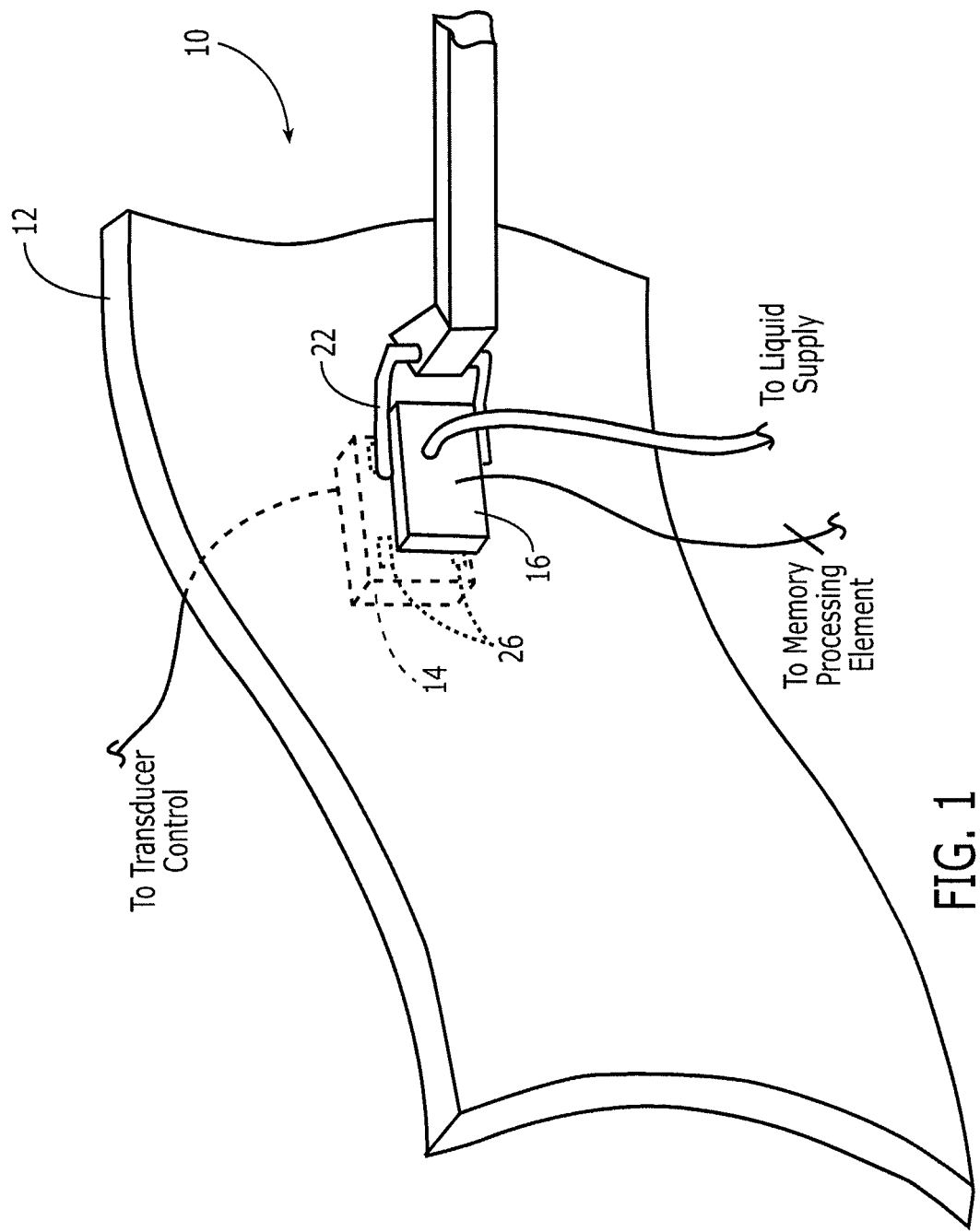
Figure 2:
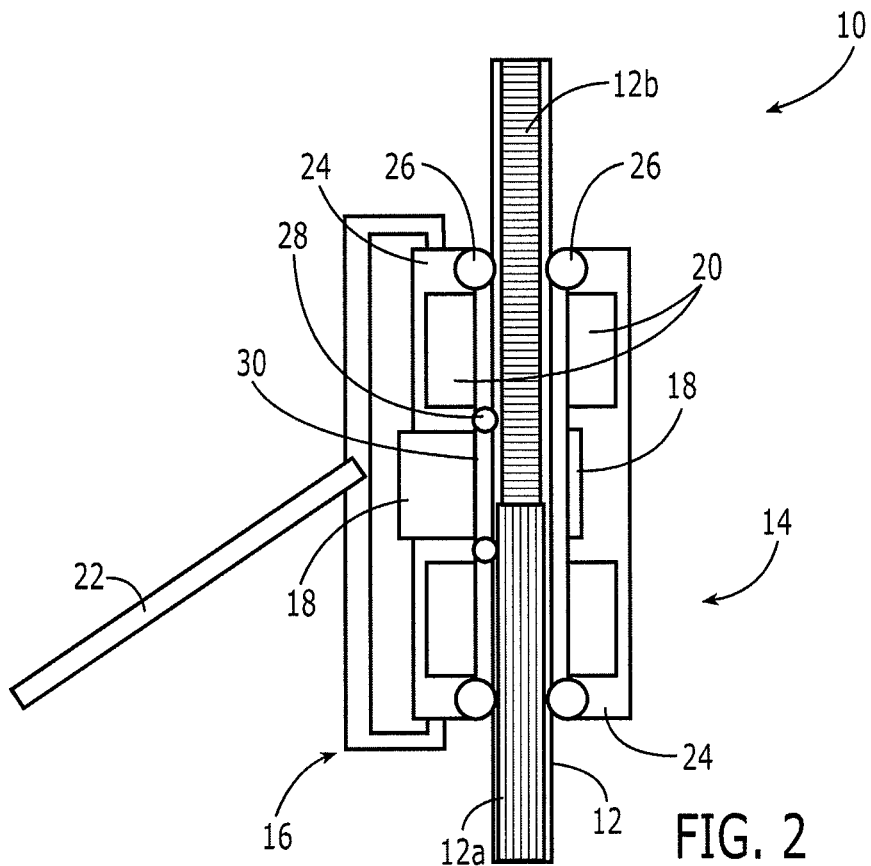
Figure 3:
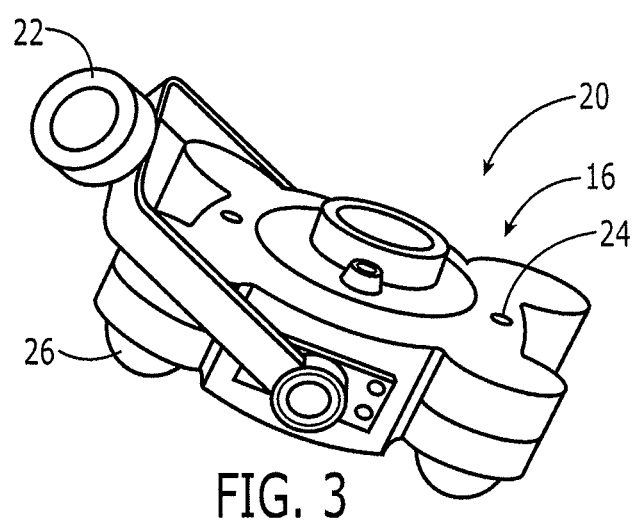
Figure 4A:
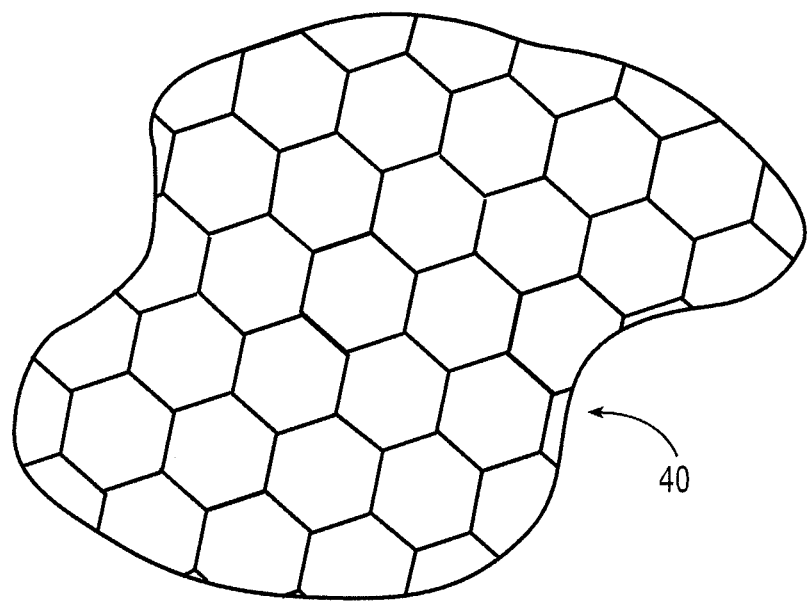
Figure 4B:
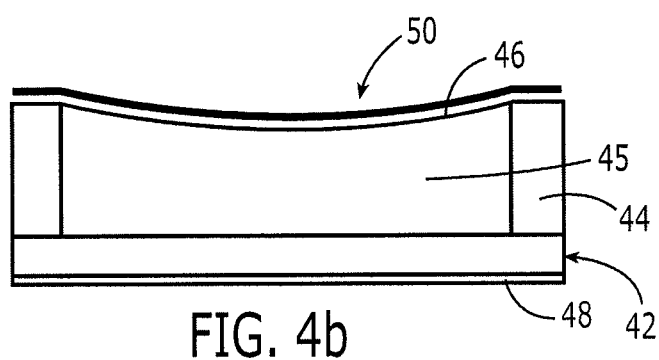
Figure 4C:
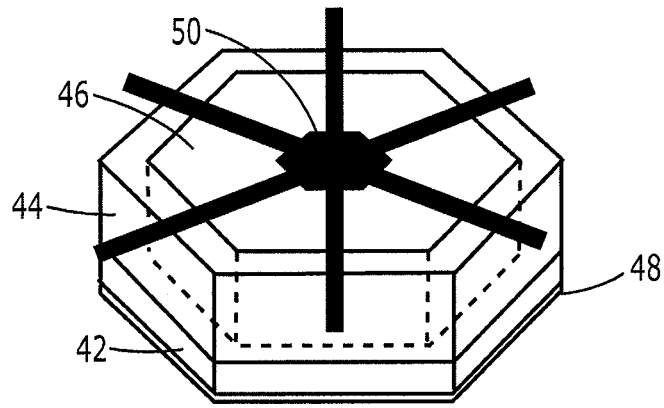

Having thus described the invention in general terms, reference will now be made to the accompanying drawings, which are not necessarily drawn to scale, and wherein:

FIG. 1 is a schematic representation of an inspection system in accordance with one embodiment to the present invention;

FIG. 2 is a cross-section of an inspection system in accordance with one embodiment to the present invention;

FIG. 3 is a perspective view of an inspection probe in accordance with one embodiment to the present invention;

FIG. 4a is a schematic representation of a portion of an array of micromachined cells of a capacitive machined ultrasonic transducer;

FIG. 4b is a cross-sectional view of a single micromachined cell of a capacitive machined ultrasonic transducer;

FIG. 4c is a perspective view of the micromachined cell of FIG. 4b; and

Figure 5:
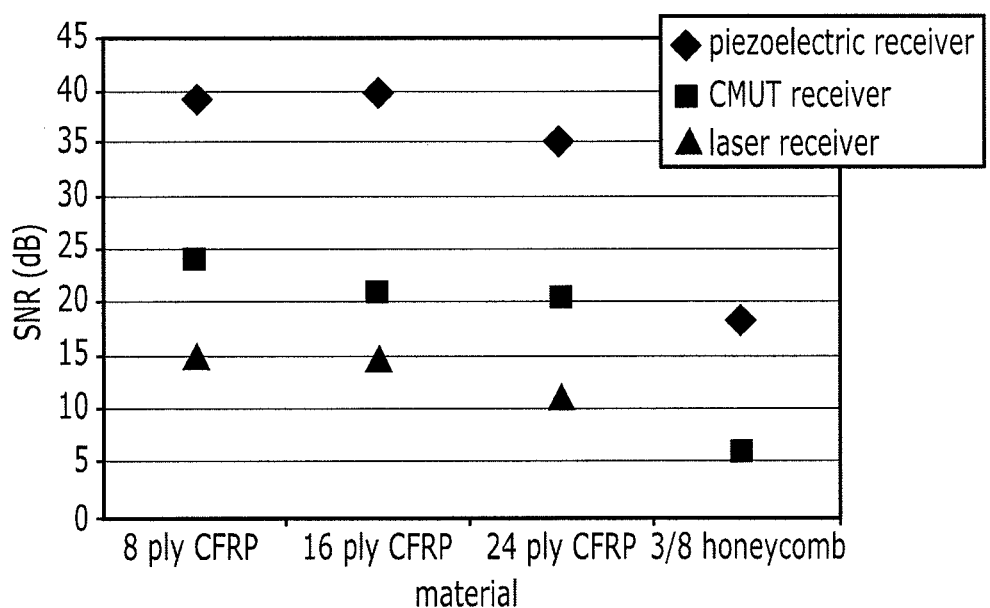

FIG. 5 is a graphical representation of the signal to noise ratio for the ultrasonic signal emitted by an air-coupled transducer and received by three different types of receivers, including a liquid-coupled piezoelectric transducer in accordance with embodiments of the present invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Referring now to FIG. 1, the inspection system 10 for inspecting a workpiece 12 according to one embodiment to the present invention is depicted. An inspection system can inspect a variety of workpieces formed of various materials. For example, the workpiece may be a composite structure having a honeycomb or foam core and/or a composite laminate structure. While a portion of a relatively simple structural panel is depicted during the course of an inspection in FIG. 1, the workpiece may have a myriad of shapes and sizes. In addition, the workpiece that is inspected may be utilized in a wide variety of applications, including vehicular applications, such as in conjunction with aircraft, marine vehicles, automobiles, spacecraft or the like, as well as other applications, such as in conjunction with buildings and other construction projects. Moreover, the workpiece may be inspected at various times, such as during manufacture, prior to assembly, following assembly or in service, as desired.

The inspection system 10 includes first and second probes 14, 16 positioned proximate opposite surfaces of the workpiece. As shown in FIG. 2, each probe includes a transducer 18 with the transducer of one probe being configured to emit ultrasonic signals and the transducer of the other probe being configured to receive the ultrasonic signals following propagation through the workpiece 12. The ultrasonic signals that are received following propagation through the workpiece can be stored along with an indication of the location at which the ultrasonic signals were received and, in some embodiments, the time at which the ultrasonic signals were received. The ultrasonic signals may be stored by a memory device that is carried by, or otherwise co-located with the respective probe or the ultrasonic signals may be stored by a memory device that is remote from the respective probe, but communicatively connected therewith, as shown in FIG. 1. By analyzing the ultrasonic signals that are received following propagation through the workpiece, the integrity of the workpiece, as well as any anomalies, delaminations or the like can be determined, along with the location of any such anomalies.

According to embodiments of the present invention, the transducers 18 of the first and second probes 14, 16 are coupled to the workpiece in different manners. In this regard, the transducer of one of the probes may be coupled to the workpiece by air, that is, a layer of air between the transducer and the respective surface of the workpiece. In contrast, the transducer of the other probe may be coupled to the workpiece by a liquid, such as water, that is positioned between the transducer and the surface of the workpiece. In order to accommodate the different coupling mechanisms, the probes may also include different types of transducers. In this regard, the air-coupled transducer may be a capacitive machined ultrasonic transducer, as described below, while the liquid-coupled transducer may be a piezoelectric transducer.

In the embodiment depicted in FIG. 1, the first probe 14 includes the air-coupled transducer that is configured to emit ultrasonic signals that are air coupled into the workpiece. In contrast, the second probe 16 includes the liquid-coupled transducer that is configured to receive the ultrasonic signals emitted by the air-coupled transducer of the first probe via a liquid couplant between the liquid-coupled transducer and the workpiece. In operation, the transducer of the first probe therefore emits ultrasonic signals that are air coupled to the workpiece. Following propagation through the workpiece, the ultrasonic signals are received by the second probe positioned proximate the second surface of the workpiece, opposite the first surface, with the ultrasonic signals being liquid-coupled from the workpiece to the transducer of the second probe.

Since one probe relies upon air coupling of the ultrasonic signals, while the other probe relies upon liquid coupling of the ultrasonic signals, the probes may be strategically placed relative to the first and second opposed surfaces of the workpiece 12 if such strategic placement would facilitate the inspection of the workpiece. In this regard, some workpieces may include one surface that may be placed into contact with liquid without any adverse effects, but an opposed surface that should not be placed into contact with liquid. In this scenario, the probe having the air-coupled transducer may be positioned proximate the surface that should not be placed into contact with liquid, while the other probe having the liquid-coupled transducer may be positioned proximate the surface that can be brought into contact with liquid. As a result of the use of probes having different coupling mechanisms, the workpiece having opposed surfaces which have different degrees of tolerance, or intolerance, to liquid may still be subject to a TTU inspection by the hybrid inspection system 10 of embodiments of the present invention. Additionally, since the probe that includes the air-coupled transducer does not require a connection to a liquid supply as does the probe that includes a liquid-coupled transducer as shown in FIG. 1, the probe that includes the air-coupled transducer may be more readily positioned proximate interior surfaces of workpieces and/or proximate the surfaces of workpieces that have more limited accessibility, than the probe that includes the liquid-coupled transducer and which requires a connection to a supply of the liquid couplant.

As described in U.S. Pat. No. 6,722,202 to James C. Kennedy, et al. and U.S. Pat. No. 7,320,249 to Gary E. Georgeson, et al. and as shown in FIG. 2, the first and second probes 14, 16 may each include magnets 20 such that the first and second probes are configured to be magnetically coupled to one another. As such, one of the probes can be driven, such as by including a mechanical connection 22 to a scanning system so as to be driven to a plurality of inspection positions relative to the workpiece 12. In contrast, the other probe may be a tracking probe that passively follows the driven probe. As such, the tracking probe may be without any independent motive force such that movement of the tracking probe is dependent upon the tracking probe passively following the driven probe as a result of the magnetic coupling therebetween. With reference to the embodiment depicted in FIG. 1, the second probe may be the driven probe and, as illustrated, may be connected through a scanning system. In contrast, the first probe may be the tracking probe which passively follows the first probe. Since the first probe need not be mechanically connected to a scanning system or any other source of motive force, the first probe can be more readily positioned proximate the surface of a workpiece that is more difficult to reach or otherwise has more restricted access than can be second probe. In this regard, since the first probe of one embodiment does not include a connection to a source of a liquid couplant and also is not physically connected to a source of motive force, the first probe may be utilized in surgical NDE applications in which the first probe is inserted through a relatively small opening in a workpiece and is positioned proximate an interior surface of a workpiece even in instances in which the accessibility to the interior surface is limited, the first probe can thereafter be moved along the workpiece so as to permit the inspection of the workpiece as result of the controlled movement of the second probe that is positioned proximate an exterior or other more accessible surface of the workpiece and the tracking of the second probe by the magnetically-coupled first probe.

As shown in FIG. 2, the inspection system 10 including one probe having an air-coupled transducer and another probe having a liquid-coupled transducer may be disposed in contact with the first and second surfaces of a workpiece 12, respectively. As shown, the workpiece may include one portion 12a having a laminate structure and another portion 12b having a honeycomb or foam core. Each probe may include a housing 24 in which the respective transducer 18 is disposed. The housing may be constructed of various materials, such as various non-magnetic materials and, in one embodiment, is constructed of Lucite® material available from E.I. DuPont Nemours and Company of Wilmington, Del. The probes may be disposed in contact with the respective surfaces of the workpiece. As shown in FIGS. 2 and 3, for example, the probes may each include wheels, skids, skis, or other contact elements 26 that extend from the housing and make contact with the respective surface of the workpiece.

As described above, each probe may include magnets 20, also typically disposed within the housing 24, for maintaining the probes directly opposed to one another as shown in FIG. 2 or otherwise in a predefined positional correspondence with one another. As a result of the magnetic coupling, this positional relationship for correspondence between the probes is maintained as the probes are moved along respective surfaces to this structure 12. As such, by tracking the position of one of the probes, the position of the other probe can be readily determined.

As shown in FIG. 2, the probe that includes the air-coupled transducer is spaced from the surface of the workpiece 12 by a layer of air. In contrast, the liquid-coupled transducer, such as a piezoelectric transducer, of the other probe includes a liquid couplant, such as water, between the transducer and the respective surface of the workpiece. In order to reduce the consumption of the liquid couplant, the probe that includes the liquid-coupled transducer may also include a seal 28, such as an O-ring or the like, that extends about the transducer and makes contact with the surface of the workpiece in order to at least partially maintain the liquid couplant 30 between the transducer 18 and the surface of the workpiece. As also shown in FIG. 2 and, in more detail, in FIG. 3, at least one of the probes, such as the probe that includes the liquid-coupled transducer, may include a mechanical connection 22 to a scanning system or other source of motive force such that the probe is driven to a plurality of predefined inspection positions relative to the workpiece with the other probe passively following and maintaining its positional relationship with respect to the driven probe as a result of the magnetic coupling therebetween.

As noted above, the air-coupled transducer may be a capacitive machined ultrasonic transducer as described, for example, by an article entitled "Development of Air-Coupled Ultrasound Transducers for Nondestructive Evaluation", by Xuefeng Wang, et al., IEEE MEMS 2008, pages 932-35, Tucson, Ariz. (Jan. 13-17, 2008). A capacitive machined ultrasound transducer may include an array of micromachined cells 40, a fragmentary portion of the array being shown in FIG. 4a and one cell of which being shown in FIGS. 4b and 4c. The array of micromachined cells may be formed upon a substrate 42, such as a silicon substrate. Each cell may be defined by an upstanding sidewall 44 that may be formed of the same material as the substrate, such as silicon, or may be formed of another, insulative material, such as silicon dioxide. As shown in FIGS. 4b and 4c, the sidewall defines an internal cavity 45. Each cell also includes a membrane 46 that extends from the sidewalls and covers and encloses the internal cavity. The internal cavity can therefore be maintained at a reduced pressure (relative to the environment). The membrane is relatively thin and flexible so as to flex in response to an ultrasound wave. The membrane may be formed of the same material as the substrate, such as silicon, or another material, such as SiNx. In order to permit the cell of a capacitive machined ultrasonic transducer to be activated, such as to emit ultrasonic signals, one electrode 48 may be applied to the substrate, while another electrode 50 may be applied to the membrane, such as a medial portion of the membrane overlying the internal cavity. The electrodes may be formed of various conductive materials, such as gold.

In order to emit ultrasonic signals, a DC bias voltage may be applied between the electrodes 48, 50 which generates an electrostatic attraction force to displace the membrane 46 toward the substrate 42. An AC driving voltage may then be superimposed upon the DC bias to cause the membrane to vibrate and emit ultrasonic waves. As shown in FIG. 1, a control line may extend from the first probe 14 in order to apply DC bias voltage and the AC driving voltage to the capacitive machined ultrasonic transducer in order to controllably generate the ultrasonic waves. Alternatively, the first probe may be wirelessly actuated, such as via a radio frequency (RF) link, thereby eliminating the need for a control line. In this regard, the first probe may include a capacitor that could be remotely charged. Upon receipt of a wireless, e.g., RF, signal indicating that ultrasonic signals should be generated, the capacitor could be at least partially discharged to the transducer in order to emit ultrasonic signals having sufficient energy. The frequency of the ultrasonic waves is dependant upon the membrane's resonance frequency as determined by its geometry and material properties. In this embodiment of the capacitive machined ultrasonic transducer described above in conjunction with FIGS. 4a-4c, the depth of the internal cavity 45 between the membrane and the substrate is about 2.5 micrometers such that the capacitive machined ultrasonic transducer emits ultrasonic signals having a frequency of at least one MHz, thereby permitting NDE with acceptable sensitivity for many inspection applications. However, the hybrid inspection system and method may operate at other frequencies, if so desired. Moreover, as compared to piezoelectric transducers, capacitive machined ultrasonic transducers have a better acoustic impedance match with air such that the air-coupled transducer has relatively high acoustic transduction efficiency.

While various types of transducers 18 may be utilized to receive the ultrasonic signals emitted by the air-coupled transducer, a hybrid inspection system 10 of one embodiment includes a liquid-coupled piezoelectric transducer which provides improved signal to noise (SNR) ratio relative to other types of transducers. As shown in FIG. 5 in comparison to a receiver having a capacitive machined ultrasonic transducer or a laser receiver, a water-coupled piezoelectric transducer exhibits a greater signal to noise ratio for its receipt of ultrasonic signals emitted by an air-coupled transducer following propagation through four different types of workpieces, namely, 8-ply, 16-ply and 24-ply carbon fiber reinforced workpieces and a ⅜ inch thick composite structure having a honeycomb core.

As described above, by utilizing both an air-coupled transducer and a liquid-coupled transducer, the hybrid inspection system 10 and method of embodiments of the present invention provide for an improved NDE of at least some workpieces 12. For example, the hybrid inspection system and method may enjoy the advantages offered by air-coupled transducers, such as the relative ease of movement, the ability to inspect workpieces within regions of limited accessibility, and the ability to inspect workpieces that are preferably not exposed to water or other liquids. However, by also employing a liquid-coupled transducer, the frequency of the ultrasonic signals can be relatively high, such as about one MHz or higher, such that the resulting NDE has sufficient sensitivity so as to be meaningful.

Many modifications and other embodiments of the inventions set forth herein will come to mind to one skilled in the art to which these inventions pertain having the benefit of the teachings presented in the foregoing descriptions and the associated drawings. For example, while the transmission-side transducer has been described to be an air-coupled transducer and the receiver-side transducer has been described to be a liquid-coupled transducer, the hybrid inspection system 10 of other embodiments may include a liquid-coupled transducer for emitting ultrasonic signals and an air-coupled transducer for receiving ultrasonic signals. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A hybrid inspection system comprising:
   a first probe comprising an air-coupled transducer configured to emit ultrasound signals and to air couple the ultrasonic signals into a workpiece, wherein the workpiece has opposed interior and exterior surfaces; and
   a second probe comprising a liquid coupled transducer configured to receive the ultrasonic signals emitted by the air-coupled transducer of the first probe via a liquid couplant between the liquid coupled transducer and the workpiece,
   wherein the air-coupled transducer of the first probe is a different type of transducer than the liquid-coupled transducer of the second probe, and
   wherein the first probe comprising the air-coupled transducer is configured to be positioned proximate the interior surface of the workpiece that has limited accessibility in that the interior surface of the workpiece is less accessible than the opposed exterior surface.

2. A hybrid inspection system according to claim 1 wherein the air-coupled transducer of the first probe comprises a capacitive machined ultrasonic transducer.

3. A hybrid inspection system according to claim 2 wherein the capacitive machined ultrasonic transducer comprises an array of micromachined cells.

4. A hybrid inspection system according to claim 1 wherein the air-coupled transducer of the first probe is configured to emit ultrasonic signals having a frequency of at last 1 MHz into the workpiece.

5. A hybrid inspection system according to claim 1 wherein the liquid coupled transducer of the second probe comprises a piezoelectric transducer.

6. A hybrid inspection system according to claim 1 wherein the first and second probes each comprise magnets such that the first and second probes are configured to be magnetically coupled to one another.

7. A hybrid inspection system according to claim 6 wherein the second probe comprises a mechanical connection to a scanning system so as to be driven to a plurality of inspection positions relative to the workpiece, and wherein the first probe is without an independent motive force such that the first probe passively follows the second probe.

8. A hybrid inspection system according to claim 1 wherein the second probe comprising the liquid-coupled transducer is configured to be positioned proximate the exterior surface of the workpiece.

9. A hybrid inspection system comprising:
   a first probe positioned proximate a first surface of a workpiece, the first probe comprising a transducer configured to emit ultrasound signals that are coupled into the workpiece, the workpiece having opposed interior and exterior surfaces; and
   a second probe positioned proximate a second surface of the workpiece, opposite the first surface, the second probe comprising a transducer configured to receive the ultrasonic signals emitted by the transducer of the first probe,
   wherein the transducer of one of the first and second probes comprises an air-coupled transducer configured to couple ultrasonic signals between the air-coupled transducer and the respective surface of the workpiece via a layer of air, and wherein the transducer of the other of the first and second probe comprises a liquid-coupled transducer configured to couple ultrasonic signals between the liquid-coupled transducer and the respective surface of the workpiece via a liquid couplant,
   wherein the air-coupled transducer of one of the first and second probes is a different type of transducer than the liquid-coupled transducer of the other of the first and second probes, and
   wherein the probe that comprises the air-coupled transducer is configured to be positioned proximate the interior surface of the workpiece that has limited accessibility in that the interior surface of the workpiece is less accessible than the opposed exterior surface.

10. A hybrid inspection system according to claim 9 wherein the air-coupled transducer comprises a capacitive machined ultrasonic transducer.

11. A hybrid inspection system according to claim 10 wherein the capacitive machined ultrasonic transducer comprises an array of micromachined cells.

12. A hybrid inspection system according to claim 9 wherein the liquid coupled transducer comprises a piezoelectric transducer.

13. A hybrid inspection system according to claim 9 wherein the first and second probes each comprise magnets such that the first and second probes are configured to be magnetically coupled to one another.

14. A hybrid inspection system according to claim 13 wherein one of the first and second probes comprises a mechanical connection to a scanning system so as to be driven to a plurality of inspection positions relative to the workpiece, and wherein the other of the first and second probes is without an independent motive force so as to passively follow the driven probe.

15. A hybrid inspection method comprising:
providing a first probe with a transducer that is of a different type than a transducer of a second probe;
emitting ultrasonic signals from the first probe positioned proximate a first surface of a workpiece with the ultrasonic signals being air coupled to the first surface of the workpiece, wherein the workpiece has opposed interior and exterior surfaces;
air coupling the ultrasonic signals form the first probe to the workpiece; and
receiving the ultrasonic signals at the second probe positioned proximate a second surface of the workpiece, opposite the first surface, following propagation through the workpiece, wherein receiving the ultrasonic signals comprises liquid coupling the ultrasonic signals from the second surface of the workpiece,
wherein the first surface to which the first probe is proximate and to which the ultrasonic signals emitted from the first probe are air coupled is an interior surface of the workpiece that has limited accessibility in that the interior surface of the workpiece is less accessible than an opposed exterior surface.

16. A hybrid inspection method according to claim 15 wherein emitting ultrasonic signals comprises emitting ultrasonic signals having a frequency of at least 1 MHz into the workpiece.

17. A hybrid inspection method according to claim 15 further comprising magnetically coupling the first and second probes.

18. An inspection method according to claim 17 further comprising moving the second probe to a plurality of inspection positions relative to the workpiece and passively following the second probe with the first probe as a result of the magnetic coupling therebetween.

19. A hybrid inspection method according to claim 15 further comprising providing the first probe within a capacitive machined ultrasonic transducer, and providing the second probe with a piezoelectric transducer.

20. A hybrid inspection method according to claim 19 further comprising providing a liquid couplant between the piezoelectric transducer and the second surface of the workpiece while receiving the ultrasonic signals.

* * * * *